United States Patent [19]

Isago et al.

[11] Patent Number: 6,136,966
[45] Date of Patent: Oct. 24, 2000

[54] PHTHALOCYANINE RADICAL ANIONS AND PROCESS FOR PRODUCING THE SAME

[75] Inventors: Hiroaki Isago; Yutaka Kagaya; Md. Hasan Zahir, all of Tsukuba, Japan

[73] Assignee: National Research Institute for Metals, Ibaraki, Japan; by said Director General

[21] Appl. No.: 09/401,720

[22] Filed: Sep. 23, 1999

[51] Int. Cl.[7] .......................... C07D 487/22; C09B 47/04
[52] U.S. Cl. ......................... 540/139; 540/122; 540/136; 540/140
[58] Field of Search ................................. 540/136, 122, 540/139, 140

[56] References Cited

U.S. PATENT DOCUMENTS 5,340,387  8/1994  Smith ..................................... 106/20 A
5,482,570  1/1996  Saurer et al. .......................... 136/255

*Primary Examiner*—John M. Ford
*Attorney, Agent, or Firm*—Wenderoth, Lind & Ponack, L.L.P.

[57] ABSTRACT

A phthalocyanine radical anion stable in ambient atmosphere, which is formed by subjecting a salt containing dihalogeno(phthalocyaninato)antimony (V) cation to a one-electron reduction. According to the present invention, a phthalocyanine radical stable in ambient atmosphere, which is expected to be developed as an n-type organic semiconductor, is provided.

10 Claims, 3 Drawing Sheets

PHTHALOCYANINE RADICAL ANIONS AND PROCESS FOR PRODUCING THE SAME

FIELD OF THE INVENTION

The present invention relates to a phthalocyanine radical anion and a process for producing the same. More specifically, the invention relates to a novel phthalocyanine radical anion which is stable in an ambient atmosphere and useful as an electronic device such as an n-type semiconductor or a photo functional material.

DESCRIPTION OF THE RELATED ART

Metallic phthalocyanine has been so far known as a substance exhibiting a p-type semiconductor property, and has attracted much interest in view of a technical development of organic semiconductor.

Organic semiconductors have been long studied because of its advantages such as diversity of compound, case in modification, cost-effectiveness, and ease in processing. Many reports have been made, especially on phthalocyanine because of its high photoconductivity, because coating or deposition enables a diverse method of production, and because it exhibits high light stability, in comparison with other organic substances. Nevertheless, the development has not been made so far to put phthalocyanine-type organic materials in practical use. This is because no stable n-type phthalocyanine semiconductor has been obtained to date, even though a large number of stable p-type phthalocyanine semiconductors have been known.

To conquer such a technical limitation, there is a phthalocyanine radical anion in which an excess electron is used as a carrier to construct an n-type semiconductor.

Phthalocyanine radical anions have been so far widely studied. However, those known so far have been problematic in that they are all extremely unstable and quickly returned to the original phthalocyanine structure through oxidation by air. Further, although it has generally been known that phthalocyanine radical anions are formed through electrolysis or a photochemical reaction, the former requires a high-quality electrolyte, and the latter requires a special device. In addition, these methods entrain a side reaction in many cases and have been inappropriate as mass-production methods. Moreover, although the reduction can be conducted with conventional reducing agents, side reactions are unavoidable. The reduction of phthalocyanine with active metals such as sodium has been long known. Nevertheless, there are at least four steps of reduction, in general, for phthalocyanine, and the stoichiometry of the starting material and the reducing agent has to be strictly controlled in order to form a specific reduction seed, involving a technical difficulty. For this reason, it has been considered to be difficult to bring such phthalocyanine radicals to practical use.

SUMMARY OF THE INVENTION

In view of the above situation, the present invention has been invented as a result of intensive study, and its main object is to provide a novel phthalocyanine radical anion stable in ambient atmosphere, which may be useful in providing an n-type semiconductor, and a process for producing the same.

BREIF DESCRIPTION OF THE DRAWINGS

The foregoing and other objects, features and advantages of the present invention will be better understood from the following detailed description, taken in conjunction with the accompanying drawings, in which.

DETAILED DESCRIPTION OF THE INVENTION

Figure 1:
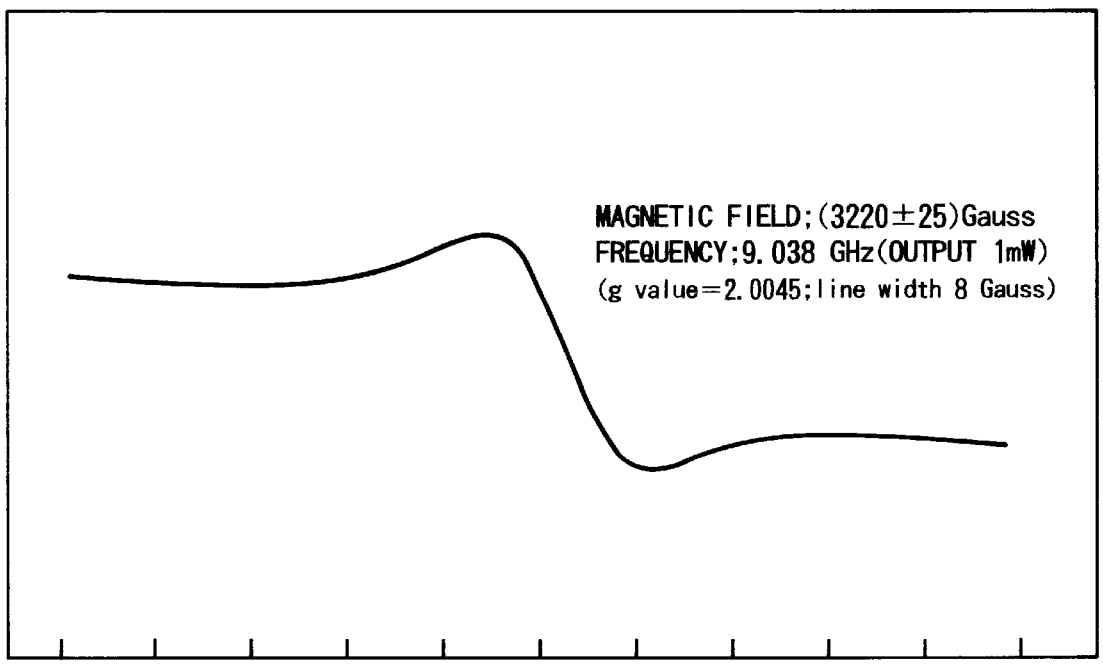
FIG. 1 is the electron spin resonance spectrum of solid dichloro (phthalocyaninato)-antimony (V) radical anion, obtained by the method of the present invention.

According to the present invention, the dihalogeno-(phthalocyaninato) antimony (V) cation formed by subjecting the phthalocyanine radical anion to one-electron reduction is, for example, represented by formula (1).

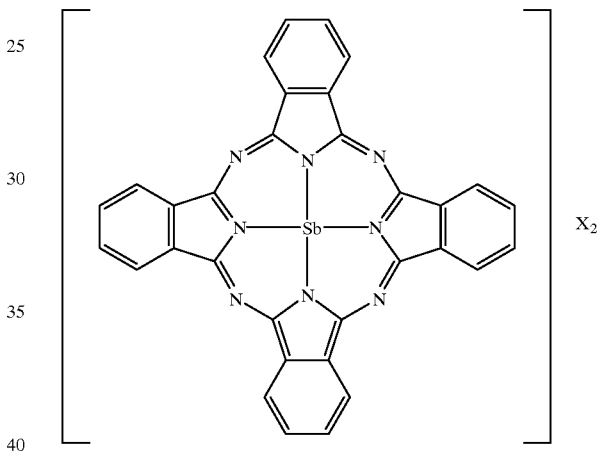

wherein X represents a halogen atom, and various substituents, such as linear or cyclic hydrocarbon groups and alkoxy groups, may be added on the phthalocyanine crown.

The one-electron reduction can be conducted chemically or electrochemically. In each case, one-electron reduction is conducted by dissolving the salt of the cation represented by formula (1) in an organic solvent.

In the present invention, dichloro(phthalocyaninato)-antimony (V) is most preferable as a dihalogeno-(phthalocyaninato)antimony (v). The embodiment of the present invention using the salt containing this cation as a starting material is described in detail below. Preferable requirements for the reaction may vary with starting materials selected.

First of all, the following requirements (1) to (5) need to be considered in the formation of the dihalogeno-(phthalocyaninato)antimony (V).

(1) reaction solvent
(2) starting material
(3) reaction temperature
(4) concentration
(5) reduction method The reaction solvent is not particularly limited so long as it can dissolve a starting material without decomposition. Specific examples thereof include dichloromethane, dichlorobenzene and chloroform. The starting material is a salt containing the dichloro(phthalocyaninato)antimony (V) cation. Counter anion for this cation in the starting material is not particularly limited. The cation-containing salt can specifically be used in the form of a hexachloroantimonate (V), a perchlorate, a tetrafluoroborate or a hexafluorophosphate.

The reaction temperature is not limited as long as it is between the freezing point and boiling point of the organic solvent used, and may be set at room temperature.

Further, because the solubility of the radical anion formed is lower than that of the starting material, it is advisable that the solution is approximately at saturation. When reduction is performed around saturated solution, the product would precipitate. More specifically, a concentration of at cast $10^{-9}$ mol/liter is favorable, but higher concentrations are more preferable. At a concentration in the range of $10^{-6}$ to $10^{-9}$ mol/liter, the radical anion formed does not precipitate. Thus, concentration becomes required to obtain the precipitate. When the concentration is less than $10^{-9}$ mols/liter, the product is below the detection limit by absorptiometry, and it is not practical. It is more favorable that the concentration of the solution be between $10^{-6}$ to $10^{-3}$ mol/liter.

The reducing agent may he, not only metallic silver, but also Al, Zn, Mg, Cu, Sn, Pb, and such other metals.

The phthalocyanine radical anion of the invention is produced using a substance having an oxidation potential in the range between 50 mV on the positive side of the first reduction potential, and 100 mV on the positive side of the second reduction potential of the (phthalocyaninato) antimony (V) cation-containing salt. At a potential more to the positive than 50 mV to the positive side of the first reduction potential of the starting material, the reduction does not proceed satisfactorily or does not proceed at all. At a potential more negative than 100 mV to the second reduction potential, the second stage reduction becomes more prominent, and unstable products of the second stage reduction emerge more. Therefore, it is more favorable that in the phthalocyaninc radical anion of the invention, the reduction is conducted using a substance which has an oxidation potential in a specific region, and which can easily be obtained and handled. Specifically, metallic silver is most favorable. However, the reducing agent does not necessarily have to be metallic silver, as long as the above conditions are satisfied.

Generally, a redox potential of a product in a solution varies with the type of solvent and reference electrode chosen. Therefore, there is no point in expressing the range of the potential suitable for the present invention, by specific values.

Furthermore, because the phthalocyaninc radical anion of the present invention is unstable in normal atmosphere unless the central metal is antimony (Sb), antimony (Sb) is an indispensable element for the invention.

With the above-mentioned requirements, only the first stage reduction can take place in the process of the present invention, due to the relationship between the reduction potential of the starting material and the oxidation potential of silver, which leads to the production of a single product, which means that the radical anion is selectively formed.

As stated above, the invention can provide a phthalocyanine radical anion stable in ambient atmosphere, which can be developed as an n-type semiconductor.

The invention is illustrated more specifically by referring to the following Example. However, the invention is not limited thereto.

EXAMPLE

Figure 2:
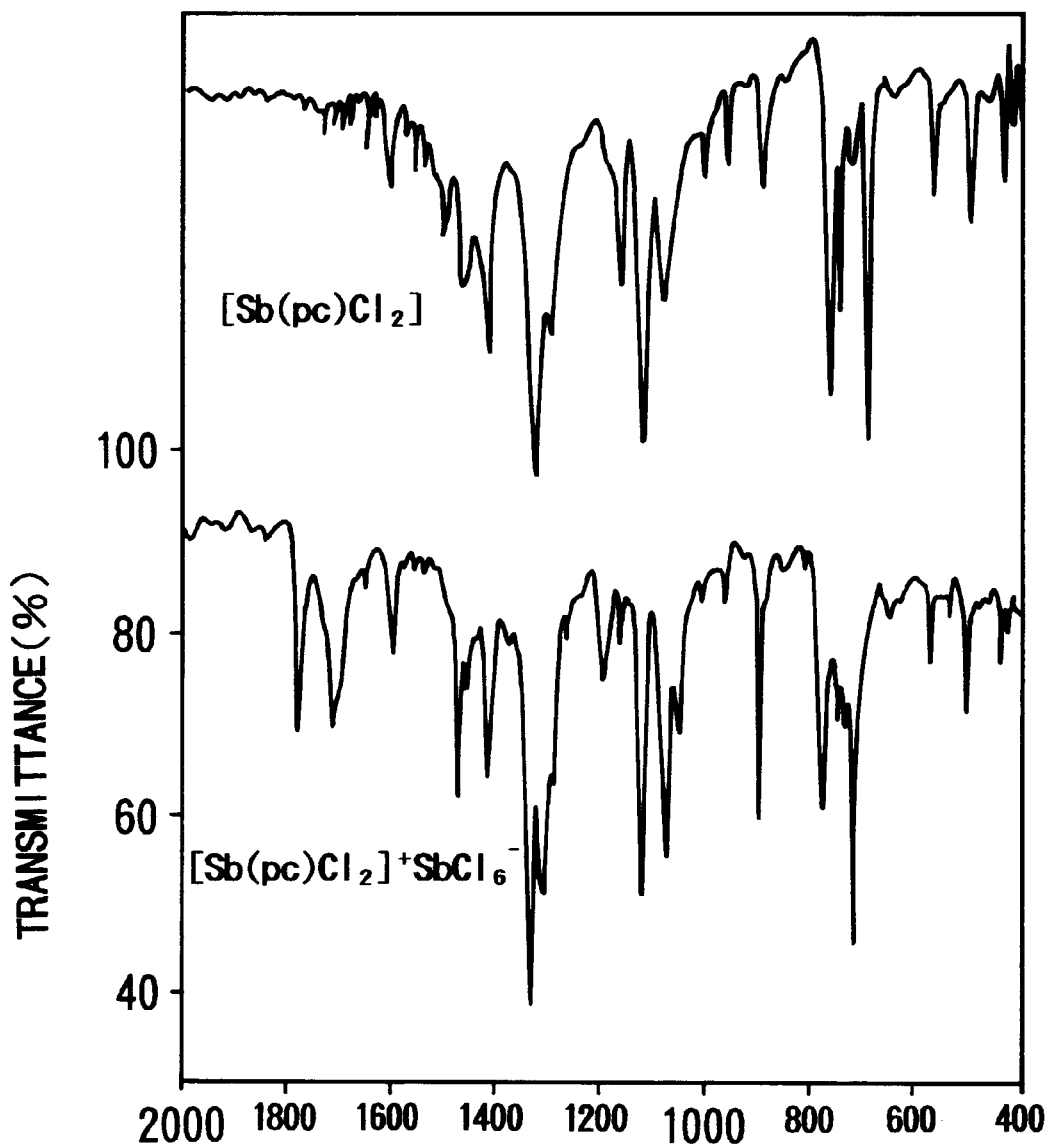
FIG. 2 is the infrared spectra of dichloro-(phthalocyaninato)antimony (V) radical anion obtained by the method of the present invention (top), and of the starting material (bottom).

Twenty milligrams of a hexachloroantimonate (V) of a dichloro (phthalocyaninato)antimony (V) cation were dissolved in 100 ml of dichloromethane (concentration approximately $1 \times 10^{-4}$ mol/liter). The mixture was stirred after adding 10 metallic silver particles (diameter approximately 3 mm). The color of the solution gradually changed from bright yellowish green to bluish purple. Approximately 2 hours later, a blue dichloro(phthalocyaninato)antimony (V) radical anion was precipitated. The solid precipitate was filtered, washed with a small amount of dichloromethane, and dried in a desiccator filled with argon. The amount of the product obtained was 8 mg. The resulting solid was identified to be the desired radical anion by electronic absorption spectroscopy and electron spin resonance (FIG. 1). Further, infrared absorption spectra (FIG. 2) verified that the amount of metal-free phthalocyanine, a product of demetallation (side reaction), was negligible.

The formation of the radical anion was also identified when metals other than silver (aluminum, zinc, magnesium, copper, tin and lead) were used. However, the formation of products by a side reaction (such as demetallation) was observed in the presence of these metals. Further, for iron and cobalt, the desired reduction did not take place, and only the side reaction occurred.

The formation of the radical anion occurred not only with hexachloroantimonate (V), but also with perchlorate, tetrafluoroborate, and hexafluorophosphate as the starting material.

Figure 3:
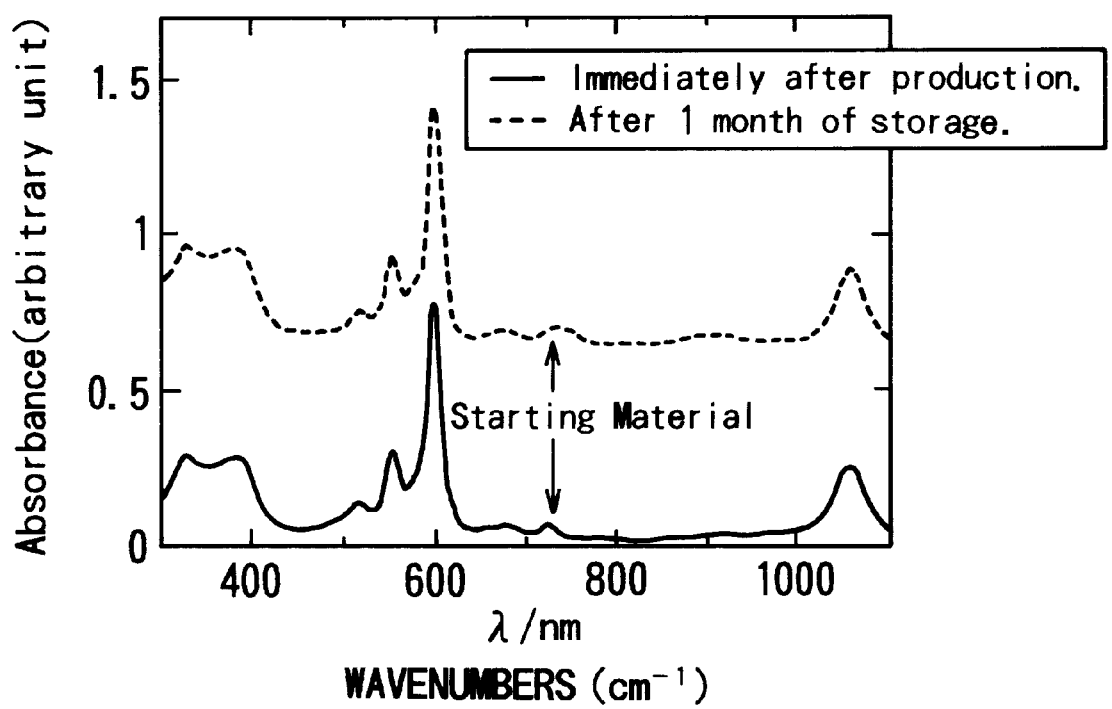
FIG. 3 is the electron absorption spectra of the dichloro (phthalocyaninato) antimony (V) radical anion obtained by the method of the present invention, immediately after its production (solid line), and after 1 month of storage (broken line).

The resulting solid was also stored for 1 month, and once again dissolved in dichloromethane. The same electron absorption spectrum as that given immediately after the production was obtained, as shown in FIG. 3. Thus, the product proved to be stable, as well.

What is claimed is:

1. A phthalocyanine radical anion stable in ambient atmosphere, which is formed by subjecting salt containing dihalogeno(phthalocyaninato)antimony (V) cation to a one-electron reduction.

2. A process for producing the phthalocyanine radical anion of claim 1, which comprises of subjecting the salt containing dihalogeno (phthalocyaninato) antimony (V) cation to a one-electron reduction.

3. The process of claim 2, wherein the salt containing dihalogeno (phthalocyaninato) antimony (V) cation is subjected to a chemical one-electron reduction in a solution.

4. A phthalocyanine radical anion stable in ambient atmosphere, which is formed by subjecting a salt containing dichloro(phthalocyaninato)antimony (V) Cation to a one-electron reduction.

5. A process for producing the phthalocyanine radical anion of claim 4, which comprises of subjecting the salt containing dichloro(phthalocyaninato)antimony (V) cation to a one-electron reduction.

6. The process of claim 5, wherein the salt containing dichloro (phthalocyaninato) antimony (V) cation is subjected to a chemical one-electron reduction in a solution.

7. The process of claim 2, 3, 5 or 6, wherein the one-electron reduction is conducted with metallic silver.

8. The process of claim 3, wherein the one-electron reduction is conducted with metallic silver.

9. The process of claim 5, wherein the one-electron reduction is conducted with metallic silver.

10. The process of claim 6, wherein the one-electron reduction is conducted with metallic silver.

* * * * *